United States Patent [19]

Akaike et al.

[11] Patent Number: 5,124,437

[45] Date of Patent: Jun. 23, 1992

[54] GALACTOSAMINE SUBSTITUTE OF POLY-OMEGA-SUBSTITUTED-L-GLUTAMIC ACID (OR ASPARTIC ACID)

[75] Inventors: Toshihiro Akaike, Tokyo; Ichirou Kitada, Chiba; Megumi Kunou, Tokyo, all of Japan

[73] Assignee: Yamanouchi Pharmaceutical Co., Ltd., Tokyo, Japan

[21] Appl. No.: 690,496

[22] Filed: Apr. 23, 1991

[30] Foreign Application Priority Data

Apr. 27, 1990 [JP] Japan .................................. 2-113681

[51] Int. Cl.$^5$ .......................... C07K 9/00; C07K 1/00; C07K 3/00; C07K 13/00
[52] U.S. Cl. ................................... 530/322; 530/345; 530/395; 530/402
[58] Field of Search .............. 514/2, 8; 530/300, 345, 530/350, 395, 402, 403, 322

[56] References Cited

FOREIGN PATENT DOCUMENTS 0042335 3/1985 Japan .

OTHER PUBLICATIONS

R. Guenin et al., *Immunobiology (Stuttgart)* 170:412–18, 1985, abstracted at *Chemical Abstracts* 105:583, #40956j, 1986.

C. J. Steer et al., *Journal of Biological Chemistry* 254:4457–4461, 10 Jun. 1979.

*Primary Examiner*—Robert A. Wax
*Assistant Examiner*—Stephen Walsh

*Attorney, Agent, or Firm*—Burgess, Ryan & Wayne

[57] ABSTRACT

A galactosamine substituted poly-w-alkyl (or benzyl)-L-glutamic acid (or aspartic acid) is provided and comprises a polypeptide having the recurring unit represented by the formula:

$$\mathrm{\{NH-CH-CO\}}_x$$
$$|$$
$$(CH_2)_n$$
$$|$$
$$COOR$$

wherein X has a value of 60 to 250; n is 1 or 2; and R represents a lower alkyl group or benzyl group, in which a part or all of the peptide in said polypeptide is substituted by an w-galactosamyl-L-glutamic acid (or aspartic acid) residue represented by the general formula:

$$-NH-CH-CO-$$
$$|$$
$$(CH_2)_n$$
$$|$$
$$CONH$$
$$|$$
$$\text{[galactosamine ring: HO, OH, OH, O, CH}_2\text{OH]}$$

wherein n is as indicated.

2 Claims, 9 Drawing Sheets

FIG. 6  PGA-GAL (85%)

PGA-GAL (70%)

PGA-GAL (60%)

PGA-GAL (40%)

GALACTOSAMINE SUBSTITUTE OF POLY-OMEGA-SUBSTITUTED-L-GLUTAMIC ACID (OR ASPARTIC ACID)

BACKGROUND OF THE INVENTION

1. Field of Industrial Application

The present invention relates to galactosamine substitutes of poly-ω-substituted-L-glutamic acid (or aspartic acid) which are useful as high molecular materials for medical use, especially as missile drug carriers.

2. Prior Art

In glycoprotein in serum, a sugar structure called sialic acid-galactose-N-acetylglucosamine is omnipresent at the termini thereof. In the late 1960's, G. Ashwell and A. Morell clarified that this triose structure was required for serum protein to be stably present in blood. When sialic acid which is present at the termini is eliminated, galactose becomes a new sugar end. Glycoprotein from which the sialic acid has been removed so that galactose has been exposed is called asialo glycoprotein. Asialo glycoprotein cannot be stably present in blood flow and rapidly disappears from blood. It is revealed that more than about 80% of the asialo glycoprotein is taken up into liver.

Specific sugar recognition receptors are present on the surface of the membrane in hepatocytes. Asialo glycoprotein is taken up into cells via this asialo glycoprotein receptor. The present inventors have made investigations, paying attention to this asialo glycoprotein receptor on the hepatocytes membrane, directed towards developing high molecular materials for drug carriers used in missile drugs, etc. As a result, it has been found that polyamino acids in which galactosamine has been introduced as a sugar residue have excellent properties. The present invention has thus been accomplished.

SUMMARY OF THE INVENTION

The present invention relates to galactosamine substitutes of poly-ω-alkyl (or benzyl)-L-glutamic acid (or aspartic acid) comprising, a polypeptide represented by general formula:

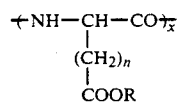

(wherein X has a value of 60 to 250; n is 1 or 2; and R represents a lower alkyl group or benzyl group), in which a part or all of the constituent peptide in the polypeptide is substituted with an ω-galactosamyl-L-glutamic acid (or aspartic acid) residue represented by general formula:

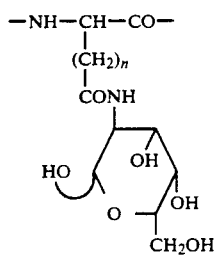

(wherein n has the same significance as described above) and, optionally with an L-glutamic acid (or aspartic acid) residue represented by formula:

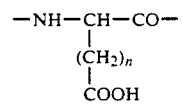

(wherein n has the same significance as described above).

DESCRIPTION OF THE PREFERRED EMBODIMENTS

The polypeptide of the present invention is further defined as follows.

Structural units
an ω-alkyl (or benzyl)-L-glutamic acid (or aspartic acid) residue:

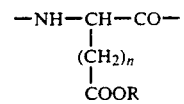

(wherein n and R have the same significances as described above);
an L-glutamic acid (or aspartic acid) residue:

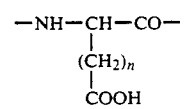

(wherein n has the same significance as described above); and,
an ω-galactosamyl-L-glutamic acid (or aspartic acid) residue:

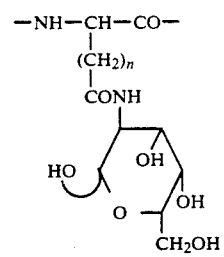

(wherein n has the same significance. as described above).
State of configuration: linear
Molecular weight: 8,000 to 71,000
Polymerization degree: 60 to 250
Ratio of the constituent units:

| | |
|---|---|
| an ω-alkyl (or benzyl)-L-glutamic acid (or aspartic acid) residue | 0–97% |
| an L-glutamic acid (or aspartic acid) residue | 0–87% |
| an ω-galactosamyl-L-glutamic acid (or aspartic acid) residue | 3–100% |

The compounds of the present invention can be synthesized by, for example, the process shown by the following equation:

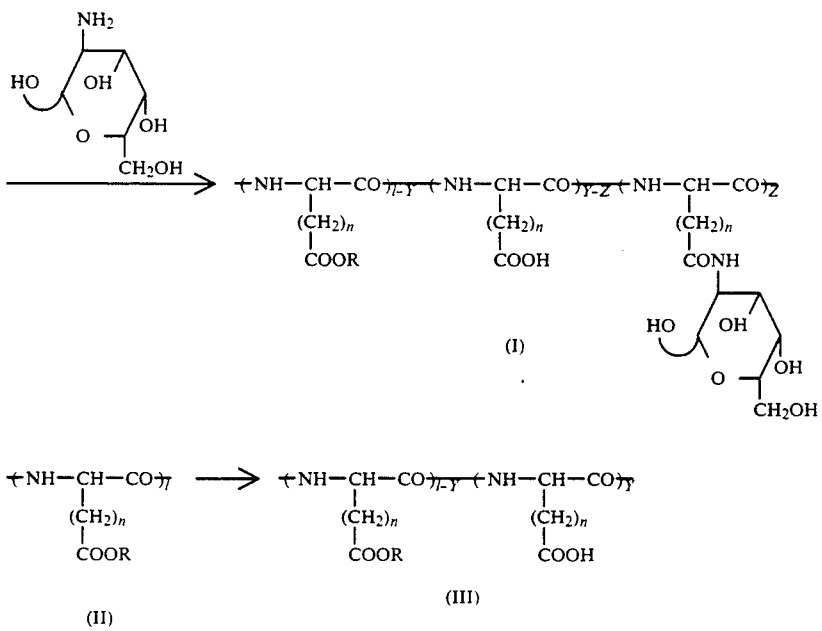

(wherein n and R have the same significances as described above; Y and Z represent a number greater than 1 and satisfy Y≧Z)

The process can be carried out by hydrolyzing the alkyl ester at the side chain of poly-ω-substituted-L-glutamic acid (or aspartic acid) (II) to obtain polymer (III) with free side chain carboxyl group (first step), and then introducing galactosamine into the side chain carboxyl group of this polymer (III) to obtain the desired compound (I) of the present invention (second step).

Hydrolysis at the first step can be readily carried out by treating poly-γ-alkyl (or benzyl)-L-glutamic acid or poly-β-alkyl (or benzyl)-L-aspartic acid with a base in an appropriate organic solvent. As the organic solvent, halogenated hydrocarbon (helix solvent) such as chloroform, dichloromethane, etc. are preferred but random coil solvents such as dichloroacetic acid, trifluoroacetic acid, etc. may also be used.

As the base, sodium hydroxide, potassium hydroxide, etc. are appropriate. These bases are added to the reaction solution generally as an aqueous solution of alcohol such as methanol, isopropyl alcohol, etc.

The reaction is carried out at about room temperature for 10 to 200 minutes.

By appropriately choosing these reaction conditions, especially reaction time, a rate of the hydrolysis may be optionally regulated.

As the poly-ω-substituted-L-glutamic acids (or aspartic acids) (II) which are used as the starting compounds at this step, compounds having a polymerization degree of about 60 to 250 are used but the starting compounds are not limited thereto. In the examples later described, for example, poly-γ-methyl-L-glutamate (simply referred to as PMLG) having a polymerization degree of approximately 100 to 200 (molecular weight of about 14,000–29,000) was used.

The second step is peptidation between the side chain carboxyl group of polyglutamic acid (or polyaspartic acid) (III) and the primary amino group of galactosamine. For this peptidation, the method for activating a carboxyl group or an amino group and the method in the presence of a condensing agent may be adopted.

Among them, for the peptidation of activating a carboxyl group, the carboxyl group of the hydrolysate (III) obtained at the first step is activated in the form of, e.g., p-nitrophenyl ester. After the activated compound is isolated, galactosamine is reacted with the compound. The reaction is carried out in a solvent such as dimethylformamide (DMF), tetrahydrofuran (THF), dimethylsulfoxide (DMSO), etc., at room temperature or with cooling. The reaction period of time is several hours to several days. A rate at which peptidation proceeds may be determined by quantitative assay of isolated p-nitrophenol associated with the reaction.

Turning next to the process using a condensing agent, the process comprises coupling the partial hydrolysate (III) with galactosamine in the presence of, e.g., N,N′-dicyclohexylcarbodiimide (DCC), 1-ethyl-3-(3-dimethylaminopropyl)carbodiimide hydrochloride (EDC), etc. The reaction conditions are identical with those of the aforesaid peptidation by activation of a carboxyl group. The formed desired product (I) can be purified by dialysis using, e.g., cellulose dialysis membrane.

It is expected that the desired compound of the present invention would have an action of recognizing target vital cells as described above. Therefore, the desired compound can be utilized in the medical field as a high molecular compound for recognizing vital cells. Furthermore, the desired compound of the present invention is degradative and water-soluble since the desired compound is a polyamino acid derivative which is a high molecular material similar to natural high molecular materials. Accordingly, the compound is preferred as a high molecular material for drug carriers used as missile drugs, etc.

Next, the affinity of the compound according to the present invention to hepatocytes is shown by animal test using rats.

Experiment

Using SD strain female rats (age of 4 to 5 weeks), rat hepatocytes were isolated by modification of so-called Seglen's perfusion method for digesting intercellular adhesive protein with enzyme. The prepared hepatocytes were suspended in ice-cold WE medium in 400,000 cells/ml. Then, 1.5 ml of the hepatocyte suspension was inoculated on each polymer-coated Petri dish (Note 1) using a disposal pipette followed by culturing at 37° C. in a carbon dioxide gas concentration of 5% for a definite period of time in a carbon dioxide gas culture device. After that, nonadhesive cells were counted to determine the rate of adhesion.

The polymers used in this experiment are the compounds of the present application, poly-γ-methyl-L-glutamate (abbreviated as PGA) and polyvinyl type polymer (polyvinylbenzyllactonamide, abbreviated as PVLA) for comparison which is conventionally known to have affinity to hepatocytes.

The state of adhesion to hepatocytes at the initial phase in each Petri dish is shown in FIG. 1. Viewing the graphs, hepatocytes have little adhesion to the main chain polymer and there is no physiological activity on the main chain itself. To the contrary, the polymer of the present invention having galactosamine on the side chain thereof shows a high rate of adhesion as in PVLA.

(Note 1) Preparation of polymer-coated Petri dish

Each sample was dissolved in milli Q water in a concentration of 0.05% (W/V). In a Petri dish 2 ml of the polymer solution was injected followed by freeze drying. Subsequently by rinsing with milli Q water 3 times and drying naturally, the polymer-coated Petri dish was prepared.

Next, with respect to the compounds of the present invention having different substitution rates of galactosamine, the rate of adhesion to each of the polymer-coated Petri dishes is shown in FIG. 2. Viewing the graphs, hepatocytes have little adhesion to the main chain polymer and to the polymer having a sugar content of 25%. It is thus considered that there would be no influence of the sugar side chain with the content of about 25%. As to the polymers having increased contents of 40%, 60%, 70% and 85%, an increased rate of adhesion to hepatic cells was noted. With respect to samples having a sugar residue of 60% or more, almost the same adhesion behavior was noted.

There are various pharmaceutical administration forms for the compounds of the present invention. For the administration of the compounds of the present invention, there are various pharmacetical forms such as nanosphere preparation, etc. Below is shown one example for preparing a nanosphere preparation.

Lipiodol, iso-butyl cyanoacrylate and a medicinal compound (a medicament) were dissolved in ethanol. On the other hand, non-ionic surfactant and a compound of the present invention were dissolved in water, and to the resultant aqueous solution was added the above ethanol solution under vigorous stirring. After lyophilization, a nanosphere preparation containing the compound of the present invention and the medicament was obtained. (cf. Ref. Int. J. Pharm. 86, 125-132 (1986)).

EXAMPLES

Next, the desired compounds of the present invention and the method for preparation are further explained with reference to the examples.

EXAMPLE 1

(1) Hydrolysis of side chain methyl ester of PMLG

In 100 ml of chloroform was dissolved 11.57 g of PMLG to prepare an 8% solution. While stirring, a mixture of 35.8 ml of 2N-sodium hydroxide, 71.5 ml of methanol and 71.5 ml of isopropyl alcohol (volume ratio, 1:2:2) was added dropwise to the solution over 15 minutes. Stirring was then continued at room temperature, whereby hydrolysis of the side chain methyl ester was carried out. In this case, the reaction was carried out by varying the stirring time. Then, the reaction mixture was neutralized with glacial acetic acid to terminate the reaction. While stirring, the reaction solution was added to 500 ml of diethyl ether to precipitate the product. The precipitates were then filtered. After washing with diethyl ether several times, a small amount of distilled water was added to the precipitates and the resulting gel was packed in a dialysis tube. Dialysis was performed at room temperature for 2 days. By subsequent freeze drying, the side chain-hydrolyzed polymer was prepared. The dialysate was appropriately exchanged.

$^1$H-NMR spectrum of the resulting side chain-hydrolyzed polymer is shown in FIG. 3. In the figure, spectra of (a), (b) and (c) were obtained by varying the reaction time with increasing time from top to bottom and the spectrum (c) shown at bottom was obtained with the reaction at room temperature for 3 days. The results reveal that the peak of the side chain methyl ester decreases in order from the top, indicating that the reaction of the side chain hydrolysis proceeds in response to the reaction time.

(2) Activation of the side chain carboxyl group

After 0.8 g ($5.9 \times 10^{-3}$ mol, value calculated from apparent molecular weight per 1 monomer unit) of the side chain partially hydrolyzed polymer and 0.55 g ($4.0 \times 10^{-3}$ mol) of p-nitrophenol were added to 20 ml of DMF, 0.82 g ($4.0 \times 10^{-3}$ mol) of DCC was added to the solution. The reaction was carried out by stirring at 0° C. for 30 minutes and then at room temperature for 2 days. Thereafter, the mixture was allowed to stand for 2 hours in a refrigerator. After thoroughly washing with DMF, water and hot ethanol in this order, the precipitates were dried in vacuum to prepare a sample. (This method is for modification of polymer having a hydrolysis rate at the side chain ester of 28.6%. In other reactions, amounts of p-nitrophenol and DCC were made 1.5 to 2 times the mol number of the carboxyl group in the polymer side chain.)

UV spectrum of the obtained compound is shown in FIG. 4. In the figure, the peak of p-nitrophenol is observed at 310 nm, confirming that p-nitrophenol was introduced into the polymer side chain.

A rate of side chain activation in this reaction (rate of introducing p-nitrophenol) was identified by measurement of UV spectrum. As a technique, there was used a method which comprises dissolving the reaction product in methanol in a concentration of 0.2 g/l, adding 0.1N potassium hydroxide to the solution, vigorously stirring the mixture for 10 minutes and measuring the absorption of p-nitrophenol in the solution appearing at 390 nm.

(3) Coupling with galactosamine (activated ester method)

In 10 ml of DMF was dissolved 0.22 g of galactosamine hydrochloride ($1.04 \times 10^{-3}$ mol). After 0.15 ml ($1.04 \times 10^{-3}$ mol) of triethylamine was added to the solution, 0.30 g ($1.84 \times 10^{-3}$ mol, value calculated from apparent molecular weight per 1 unit) was added to the mixture. The reaction was carried out at room temperature for 2 days. Then the solution containing the precipitates was dialyzed (2 days) and then freeze dried to prepare a sample (charged amounts given herein are for the sample obtained by activation of the side chain using the polymer having a side chain hydrolysis rate of 28.6% described above. For other samples, about two-fold amounts of sugar and triethylamine were used in response to the rate of activation of the side chain).

(Method using condensing agent)

After 0.45 g of PGA was dissolved in an aqueous solution, galactosamine (Gal-NH$_2$) was then dissolved in 1.5, 1, 0.75, 0.5 and 0.25-fold mols of the side chain carboxyl group. A pH of the solution was adjusted to 4.7 with 0.1N hydrochloric acid. An aqueous solution having pH of 4.7 in which EDC was dissolved in 1.5-fold mol of the galactosamine used in the solution was dropwise added to the solution at 0° C. over 8 hours. Subsequently, the reaction was carried out at room temperature for 24 hours and then dialyzed for 2 days. By freeze drying, samples were prepared.

The measurement results of $^1$H-NMR spectrum of the resulting compound (PGA-Gal) obtained in these reactions are shown in FIG. 5. As is clear from the figure, the peak of the sugar was observed at about 4 ppm in each sample, confirming that the sugar was introduced into the polymer side chain.

The measurement results of $^1$H-NMR spectrum of each of the resulting galactosamine substitute compound (PGA-Gal) obtained in the above condensing reaction in the case of the galactosamine being used in 1.5, 1, 0.75 and 0.5 mols of the side chain carboxyl group for coupling are shown in FIG. 6, FIG. 7, FIG. 8 and FIG. 9, respectively. As is clear from the figure, the PGA-Gal compound-85 (galactosamine substitution rate of 85), the PGA-Gal compound-70 (galactosamine substitution rate of 70), the PGA-Gal compound-60 (galactosamine substitution rate of 60) and the PGA-Gal compound-40 (galactosamine substitution rate of 40) were obtained according to the used amount of galactosamine.

Figure 1:
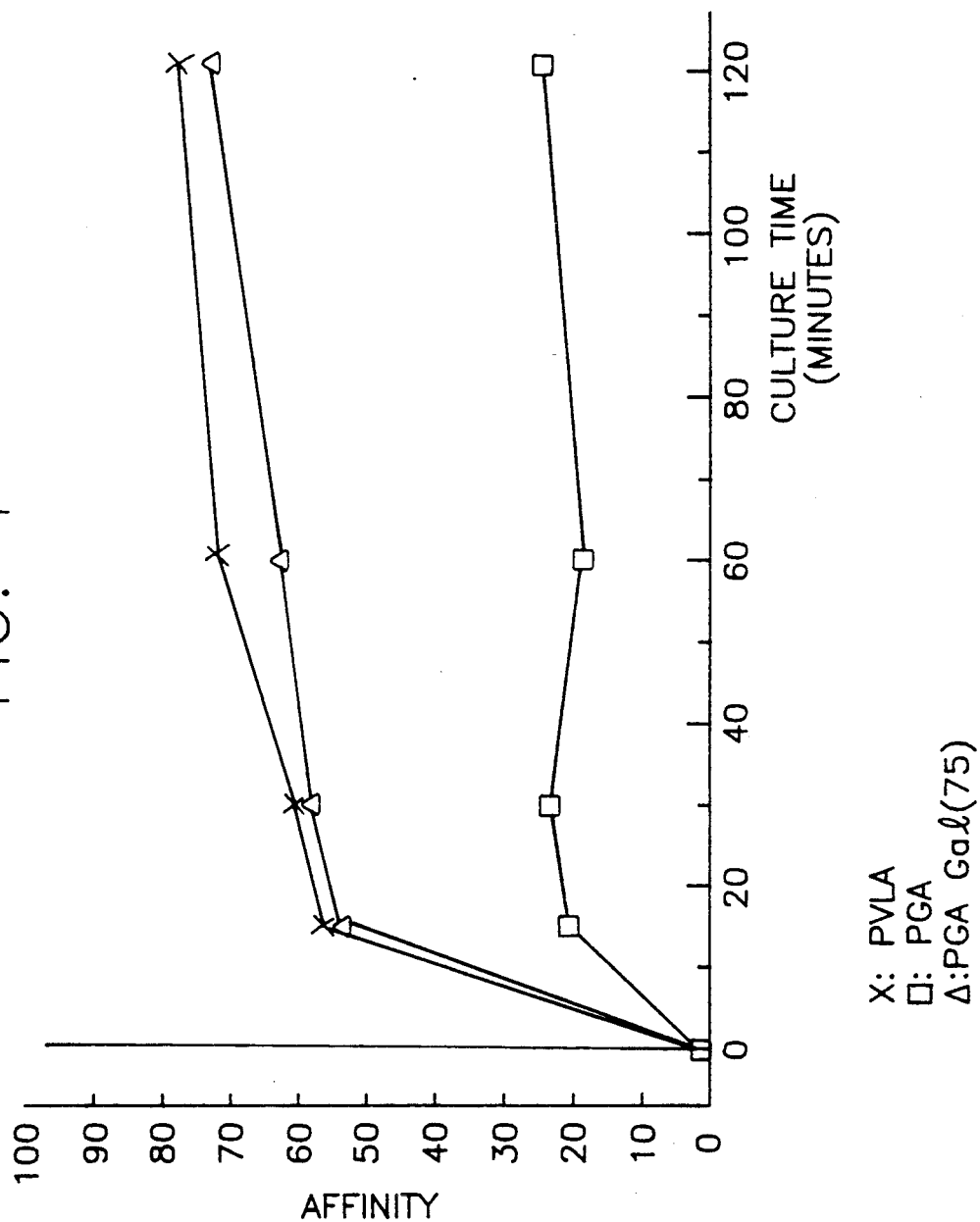
FIG. 1 shows affinity of the compound of the present invention (PGA-Gal: substitution rate of 75), starting compound (PGA) and control (PVLA) to rat hepatocytes.
Figure 2:
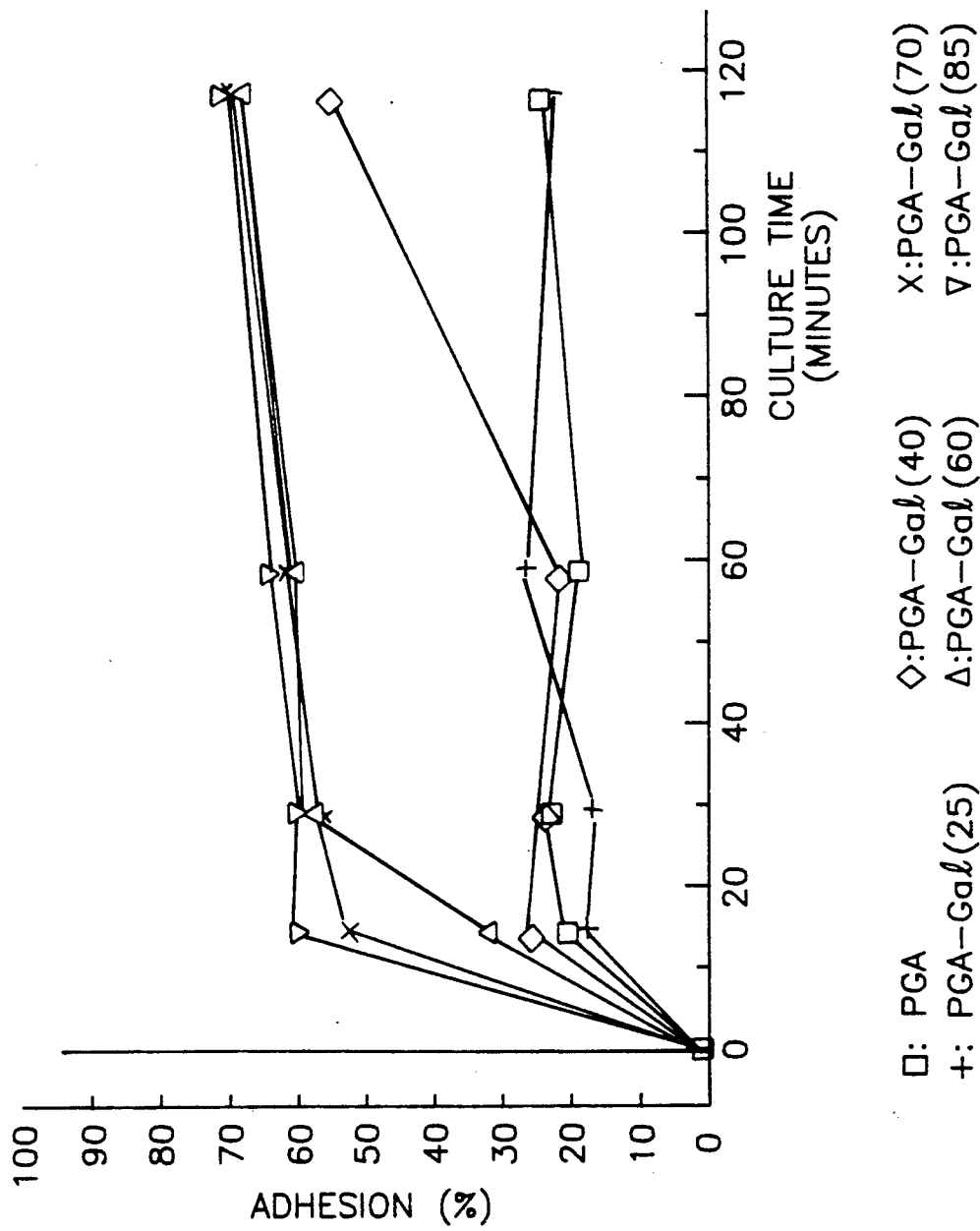
FIG. 2 shows a difference in adhesion rate of the compounds of the present invention having different sugar contents to hepatic cells in terms of each culturing time.
Figure 3:
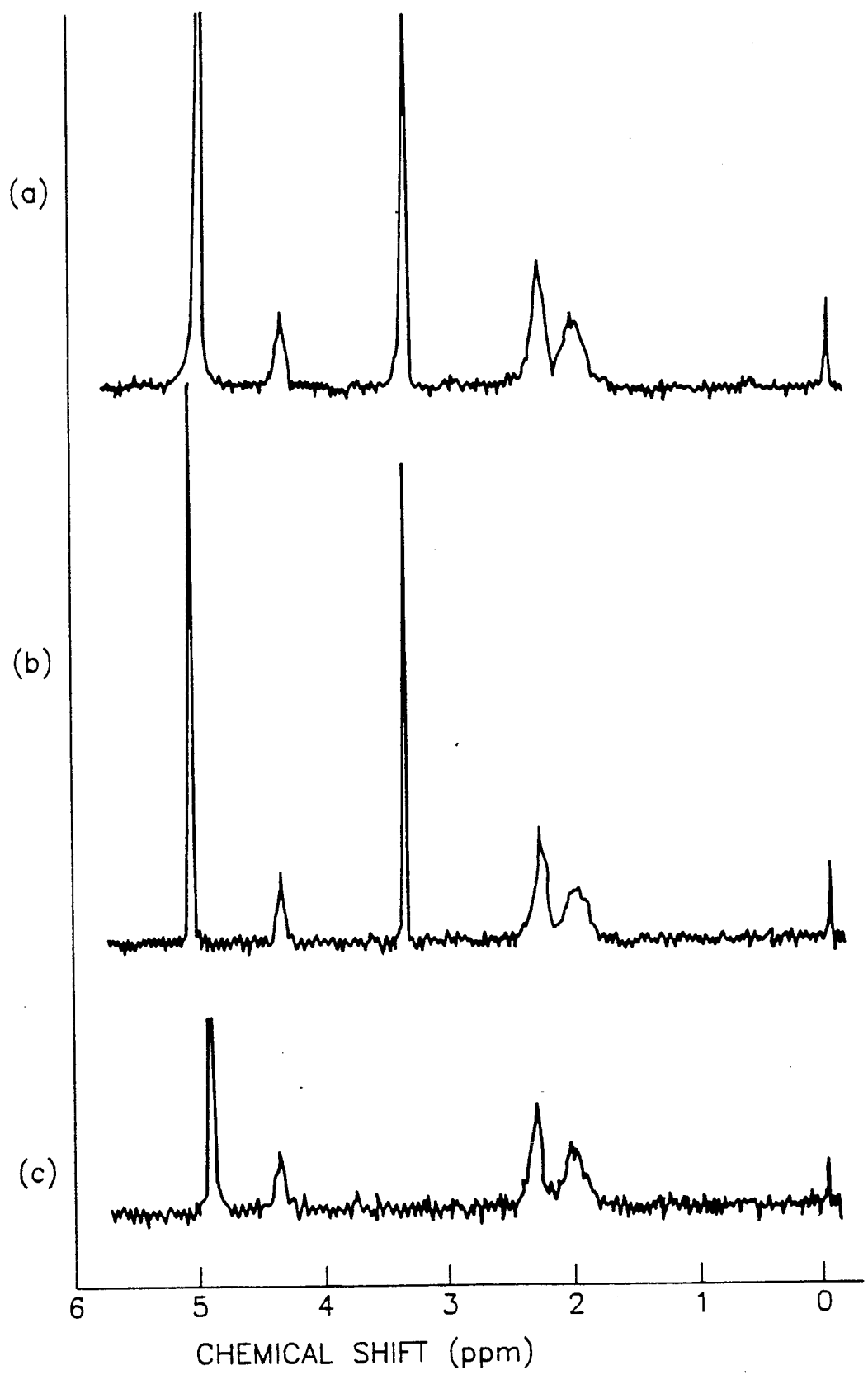
FIG. 3 is $^1$H-NMR spectrum indicating the progress of hydrolysis of PMLG at the side chain methyl ester. In the figure, (c) is obtained by measurement of the product after reacting at room temperature for 3 days.
Figure 4:
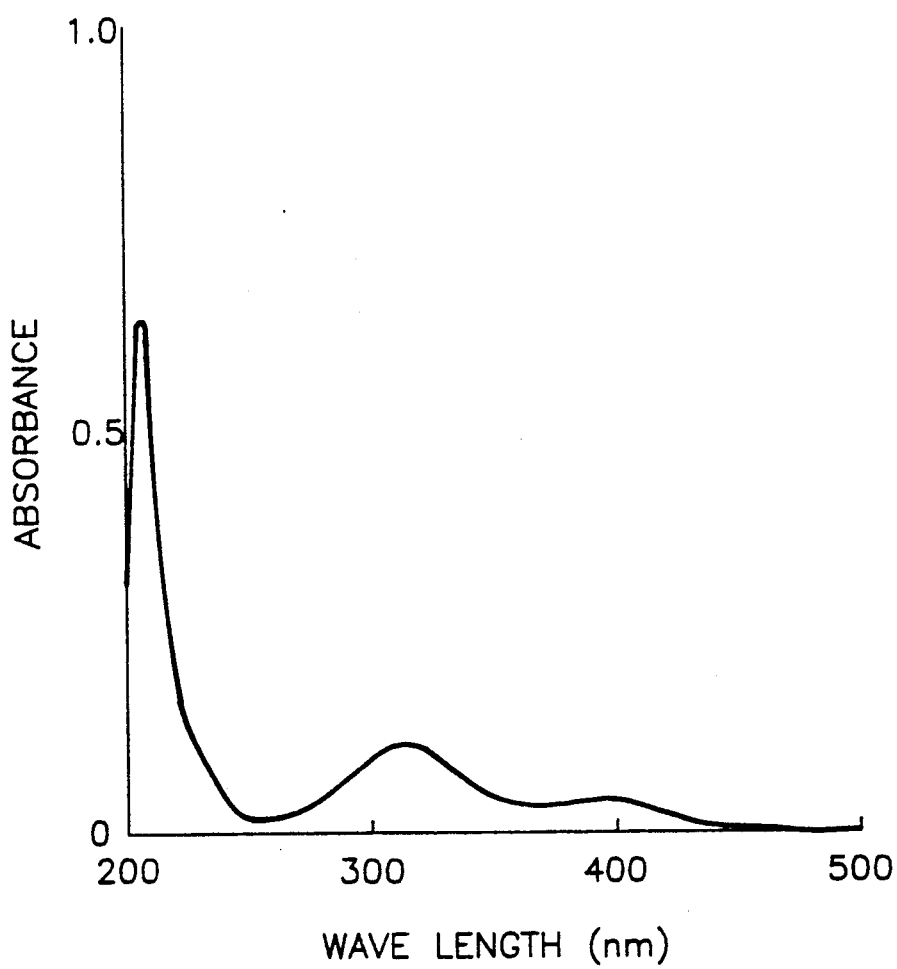
FIG. 4 shows UV spectrum of the compound obtained in Example 1 (2).
Figure 5:
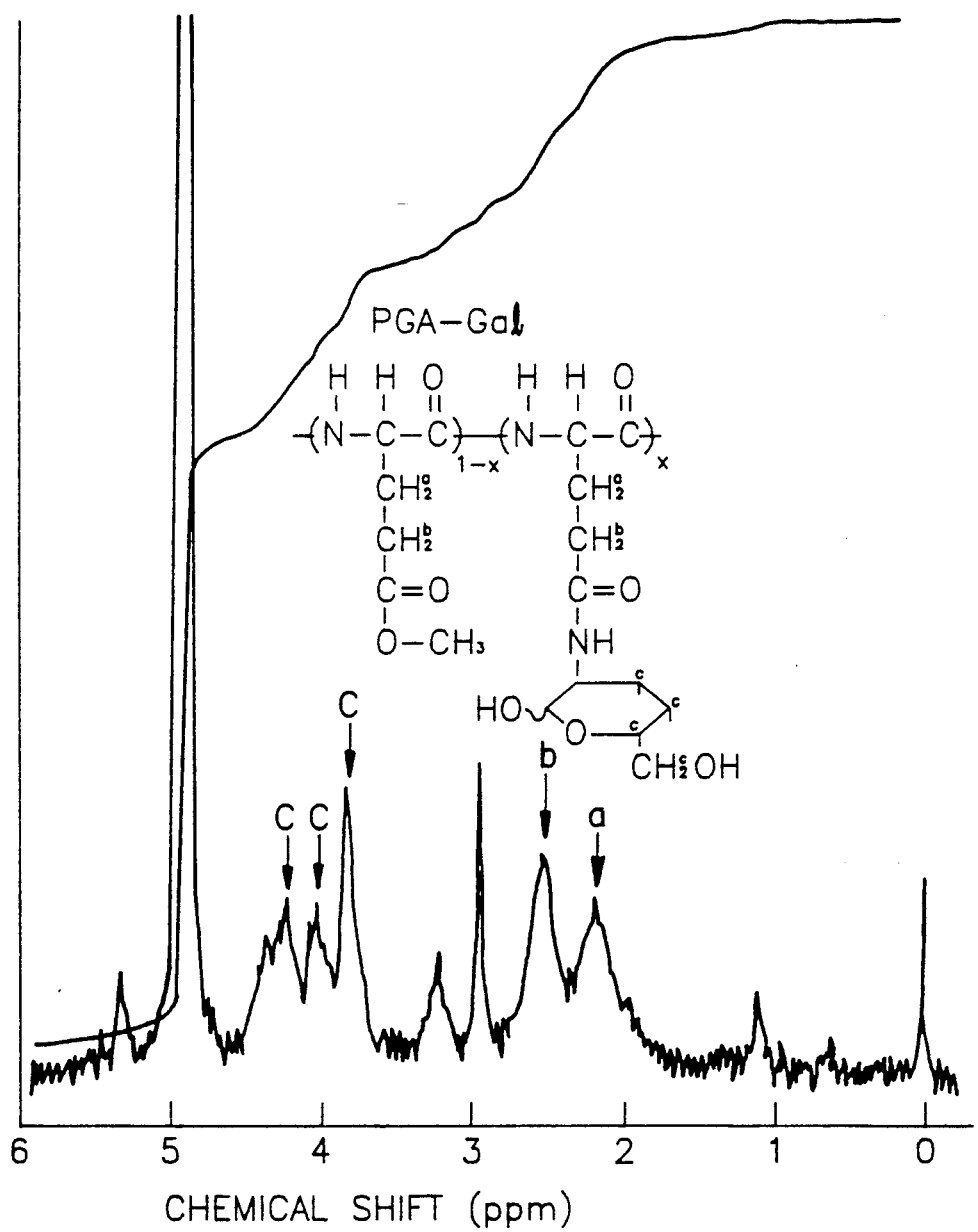
FIG. 5 shows $^1$H-NMR spectrum of the compound obtained in Example 1 (3).
Figure 6:
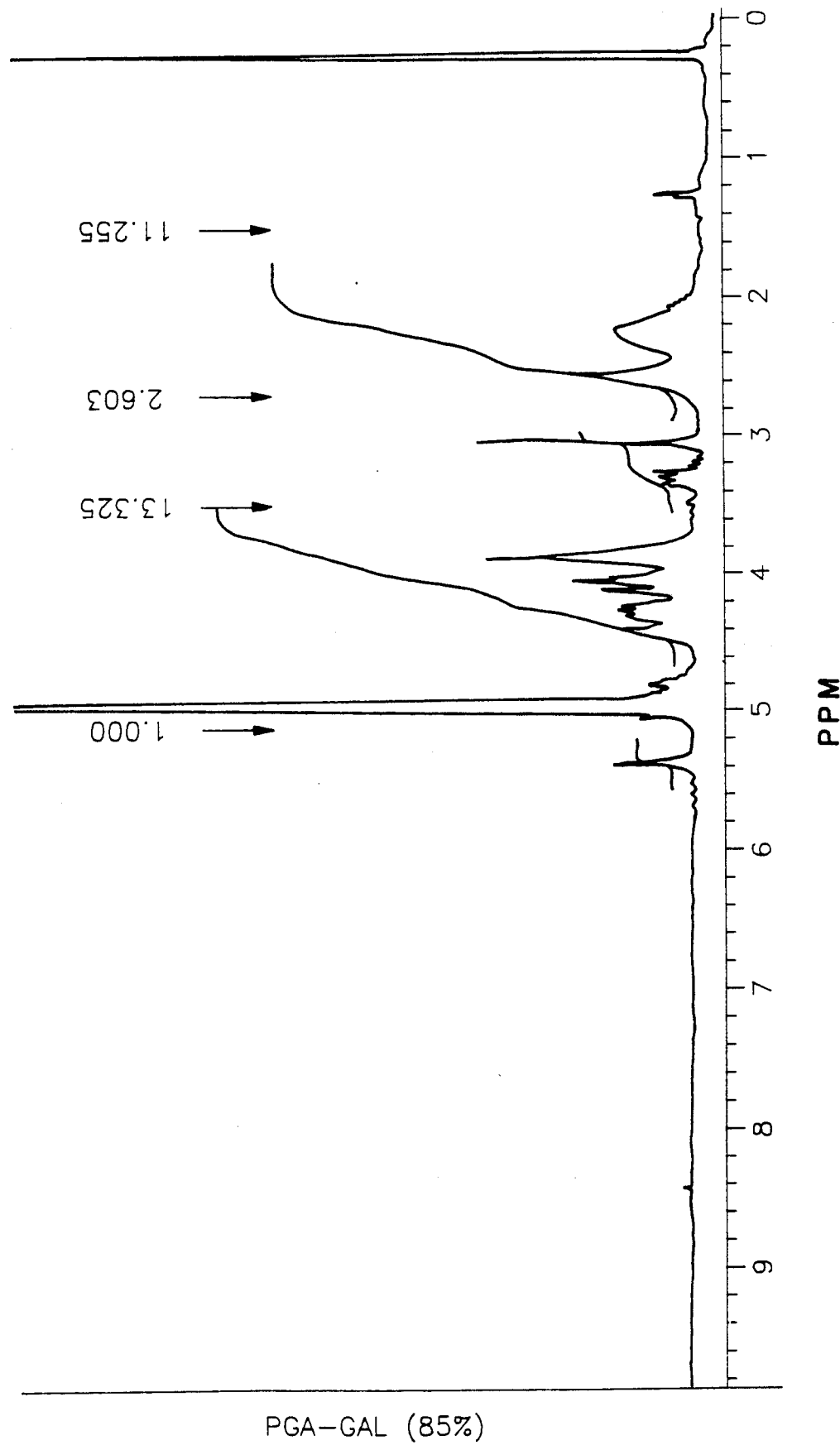
FIG. 6 shows $^1$H-NMR spectrum of the PGA-Gal compound-85.
Figure 7:
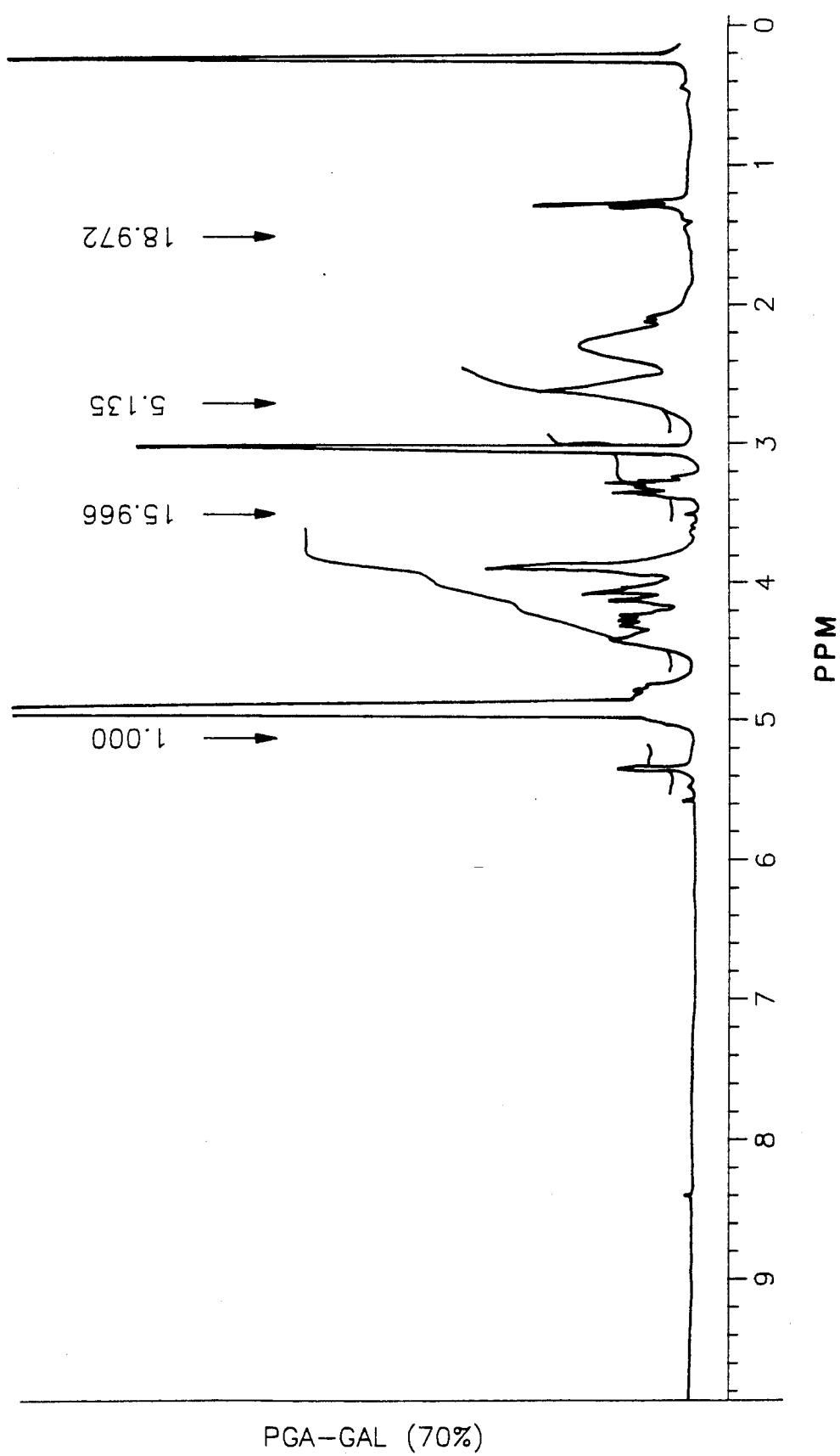
FIG. 7 shows $^1$H-NMR spectrum of the PGA-Gal compound-70.
Figure 8:
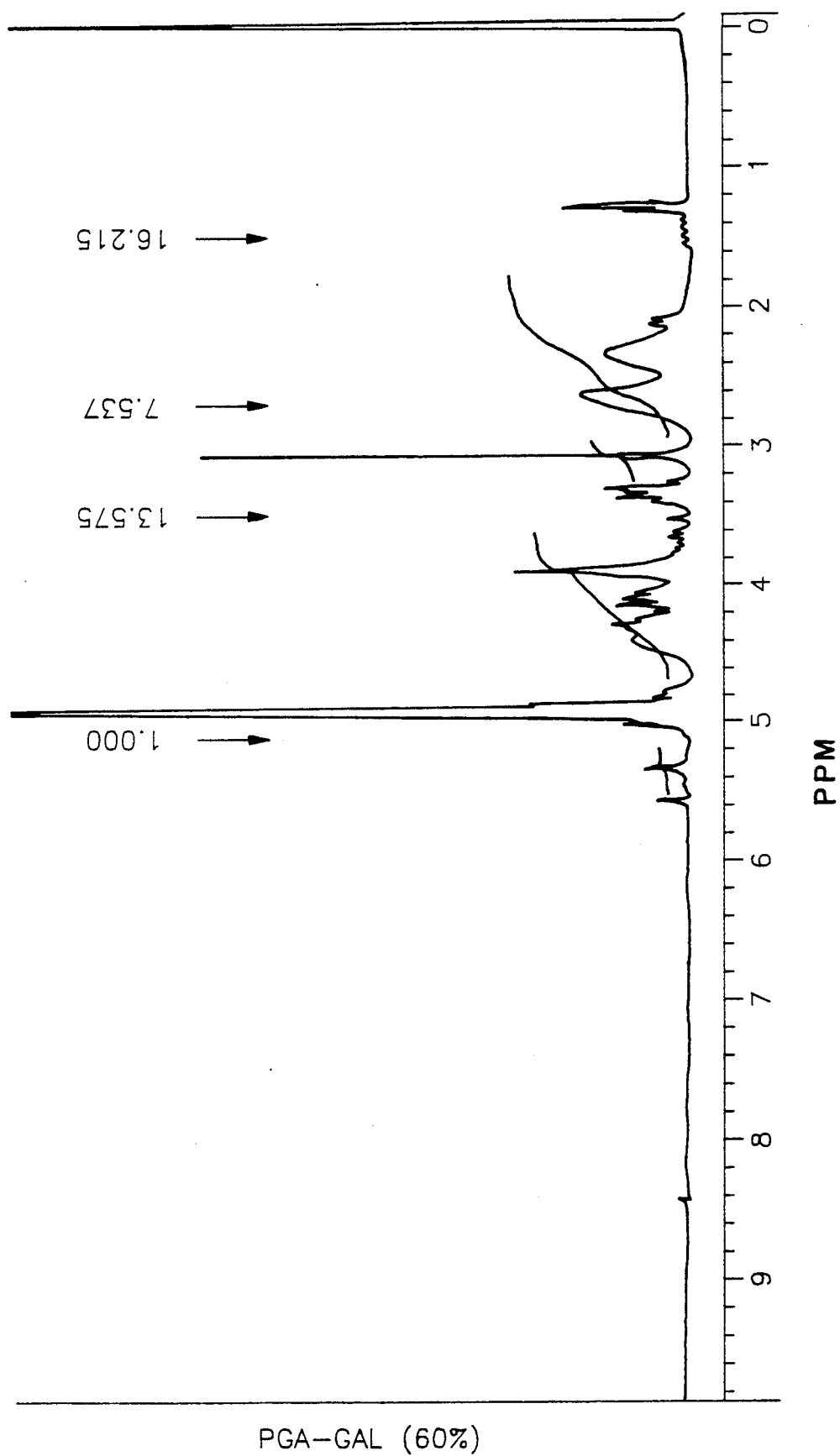
FIG. 8 shows $^1$H-NMR spectrum of the PGA-Gal compound 60.
Figure 9:
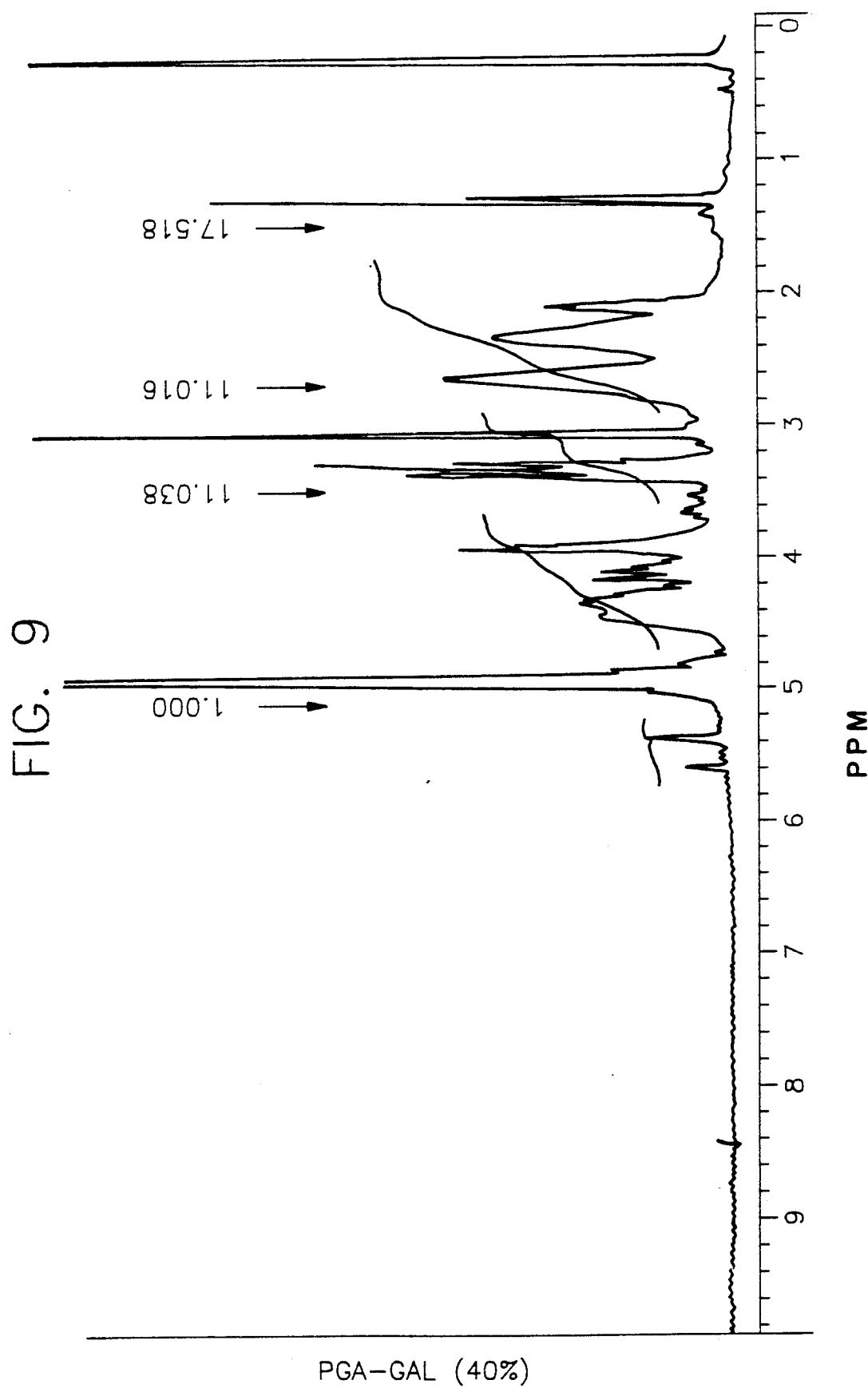
FIG. 9 shows $^1$H-NMR spectrum of the PGA-Gal cojmpound 40.

We claim:

1. A galactosamine substituted poly-ω-alkyl or benzyl-L-glutamic acid or aspartic acid comprising a polypeptide having a recurring unit represented by the general formula:

$$\mathrm{\{NH-CH-CO\}}_x$$
$$|$$
$$(CH_2)_n$$
$$|$$
$$COOR$$

wherein X has a value of 60 to 250; n is 1 or 2; and R represents a $C_{1-4}$ alkyl group or benzyl group, in which a part or all of said recurring units in said polypeptide are substituted by an ω-galactosamyl-L-glutamic acid or aspartic acid residue represented by the formula:

$$-NH-CH-CO-$$
$$|$$
$$(CH_2)_n$$
$$|$$
$$CONH$$
$$|$$
(galactosamine ring with HO, OH, OH, CH$_2$OH)

wherein n has the same value as described above.

2. A partially galactosamylated ω-alkyl or benzyl-L-glutamic acid or aspartic acid linear polymer comprising, as recurring units, an ω-alkyl or benzyl-L-glutamic acid or aspartic acid residue:

$$\mathrm{\{NH-CH-CO\}}$$
$$|$$
$$(CH_2)_n$$
$$|$$
$$COOR$$

wherein n is 1 or 2 and R represents a $C_{1-4}$ alkyl group or benzyl group;

and L-glutamic acid or aspartic acid residue:

$$-NH-CH-CO-$$
$$|$$
$$(CH_2)_n$$
$$|$$
$$COOH$$

wherein n has the same significance as described above; and, an ω-galactosamyl-L-glutamic acid (or aspartic acid) residue:

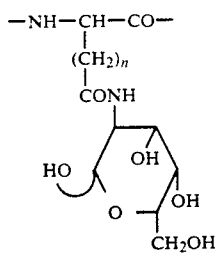
wherein n has the same significance as described above, and said polymer having from 60 to 250 recurring units, a molecular weight of 8,000 to 71,000 and the following ratio of the respective recurring units:
an ω-alkyl or benzyl-L-glutamic acid or aspartic acid residue: 0–97%
an L-glutamic acid or aspartic acid residue: 0–87% and
an ω-galactosamyl-L-glutamic acid or aspartic acid residue: 3–100%.
* * * * *